US006500807B1

(12) United States Patent
Platt et al.

(10) Patent No.: US 6,500,807 B1
(45) Date of Patent: Dec. 31, 2002

(54) MODIFIED PECTIN AND NUCLEIC ACID COMPOSITION

(75) Inventors: David Platt, Newton, MA (US); Yan Chang, Chestnut Hill, MA (US)

(73) Assignee: Safescience, Inc., Boston, MA (US)

( * ) Notice: Subject to any disclaimer, the term of this patent is extended or adjusted under 35 U.S.C. 154(b) by 0 days.

(21) Appl. No.: 09/495,675

(22) Filed: Feb. 1, 2000

Related U.S. Application Data
(60) Provisional application No. 60/118,244, filed on Feb. 2, 1999.

(51) Int. Cl.$^7$ .............................................. A01N 43/04
(52) U.S. Cl. ........................... 514/44; 514/54; 536/23.1
(58) Field of Search ................... 514/44, 54; 435/320.1; 536/23.1

(56) References Cited

U.S. PATENT DOCUMENTS

| | | | |
|---|---|---|---|
| 4,167,447 A | 9/1979 | Masri et al. | 435/178 |
| 4,647,536 A | 3/1987 | Mosbach et al. | 435/177 |
| 4,713,249 A | 12/1987 | Schroder | 424/488 |
| 4,744,933 A | 5/1988 | Rha et al. | 264/4.3 |
| 4,803,168 A | 2/1989 | Jarvis, Jr. | 435/240 |
| 4,808,707 A | 2/1989 | Daly et al. | 536/3 |
| 4,895,724 A | 1/1990 | Cardinal et al. | 424/418 |
| 5,015,476 A | 5/1991 | Cochrum et al. | 424/423 |
| 5,116,747 A | 5/1992 | Moo-Young et al. | 435/178 |
| 5,160,745 A | 11/1992 | DeLuca et al. | 424/487 |
| 5,183,690 A | 2/1993 | Carr et al. | 427/213 |
| 5,460,831 A | 10/1995 | Kossovsky et al. | 424/493 |
| 5,462,751 A | 10/1995 | Kossovsky et al. | 424/494 |
| 5,569,483 A | 10/1996 | Timonen et al. | 426/658 |
| 5,594,136 A | 1/1997 | Sessler et al. | 540/472 |
| 5,635,207 A | 6/1997 | Grinstaff et al. | 424/450 |
| 5,635,493 A | 6/1997 | Vournakis et al. | 514/55 |
| 5,639,473 A | 6/1997 | Grinstaff et al. | 424/450 |
| 5,648,252 A | 7/1997 | Dumitriu et al. | 435/179 |
| 5,651,980 A | 7/1997 | Lanza et al. | 424/424 |
| 5,665,383 A | 9/1997 | Grinstaff et al. | 424/450 |
| 5,686,115 A | 11/1997 | Vournakis et al. | 424/488 |
| 5,773,033 A | 6/1998 | Cochrum et al. | 424/530 |
| 5,827,707 A | 10/1998 | Lamberti | 435/178 |
| 5,858,392 A | 1/1999 | Dumitriu et al. | 424/443 |
| 5,858,746 A | 1/1999 | Hubbell et al. | 435/177 |
| 5,871,985 A | 2/1999 | Aebischer et al. | 435/178 |
| 5,879,713 A | 3/1999 | Roth et al. | 424/489 |
| 5,895,784 A | 4/1999 | Raz et al. | 514/54 |
| 5,900,238 A | 5/1999 | Gombotz et al. | 424/184.1 |
| 5,972,707 A | 10/1999 | Roy et al. | 435/455 |

OTHER PUBLICATIONS

US 5,849,884, 12/1998, Woiszwillo et al. (withdrawn)
Anderson, "Human gene therapy", Nature, 392(Supp.): 25–30, Apr. 1998.*
Verma and Somia, "Gene therapy–promises, problems and prospects", Nature, 389:239–242, Sep. 1997.*
www.harcourt.com/dictionary, Academic Press Online Dictionary of Science and Technology, accessed by PTO Jun. 5, 2000.*
Wakerly et. al.; Studies on Amidated Pectins as Potential Carriers in Colonic Drug Delivery, 1997, J. Pharm. Pharmacol 49: 622–625.*
Adkin et. al.; The use of scintigraphy to provide "proof of conceptaaaa" for novel polysaccharide preparations designed for colonic drug delivery, 1997, Pharm Res.: 103–107 Abstract.*
Wakerly et. al.; Pectin/ethylcellulose film coating formulations for colonic drug delivery, 1996, Pharm Res.: 1210–2 Abstract.*
Leong et al. "DNA–polycation nonospheres as non–viral gene delivery vehicles" Journal of Controlled Release 53 (1998) 183–193.
Crystal et al. "Phase I Study of Direct Administration of a Replication Deficient Adenovirus Vector Containing the *E. coli* Cytosine Deaminase Gene to Metastatic Colon Carcinoma of the Liver in Association with the Oral Administration of the Pro–Drug 5–Fluorocytosine" Human Gene Therapy 8:985–10001 (May 20, 1997).
Xu et al. "Parenteral Gene Therapy with p53 Inhibits Human Breast Tumors In Vivo Through a Bystander Mechanism Without Evidence of Toxicity" Human Gene Therapy 8:177–185 (Jan. 20, 1997).
Pienta et al. "Inhibition of Spontaneous Metastasis in a Rat Prostate Cancer Model by Oral Administration of Modified Citrus Pectin" Journal of the National Cancer Institute, vol. 87, No. 5, pp. 348–353 (Mar. 1, 1995).
Tanaka et al. "Viral Vector–targeted Antiangiogenic Gene Therapy Utilizing an Angiostatin Complementary DNA" Cancer Research 58, 3362–3369 (Aug. 1, 1998).
Zrihan–Licht et al. "Csk Homologous Kinase, a Novel Signaling Molecule, Directly Associates with the Activated ErbB–2 Receptor in Breast Cancer Cells and Inhibits Their Proliferation" The Journal of Biological Chemistry, vol. 273, No. 7, pp. 4065–4072 (Feb. 13, 1998).
Roy et al. (1999) Oral gene delivery with chitosan–DNA nanoparticles generates immunologic protection in a murine model of peanut allergy.
Nature Medicine, vol. 5, No. 4, pp. 387–391.

* cited by examiner

*Primary Examiner*—Deborah Crouch
*Assistant Examiner*—Joseph Woitach
(74) *Attorney, Agent, or Firm*—Gifford, Krass, Groh, Sprinkle, Anderson & Citkowski, P.C.

(57) ABSTRACT

According to the present invention, there is provided a gene therapy material which includes a nucleic acid material and a carbohydrate wherein the carbohydrate preferably is a modified pectin. Also in accordance with the present invention, there is provided a gene therapy material including a nucleic acid material, a carbohydrate material associated with the nucleic acid material, and a protective coating disposed about the carbohydrate material.

8 Claims, No Drawings

MODIFIED PECTIN AND NUCLEIC ACID COMPOSITION

RELATED APPLICATION

This application claims priority of U.S. Provisional Application Serial No. 60/118,244 filed Feb. 2, 1999.

TECHNICAL FIELD

The present invention generally relates to gene therapy. More particularly, the present invention relates to a gene therapy material which includes a nucleic acid material and a carbohydrate as a delivery vehicle.

BACKGROUND OF THE INVENTION

Gene therapy involves the use of genetic material as a therapeutic agent. More specifically, in gene therapy a natural or synthetic gene or an analog thereof is introduced into a patient's tissue, where activation of the gene produces a therapeutic effect. Gene therapy shows great promise for curing various metabolic diseases resulting from a deficiency of, or malformation of, enzymes, proteins, neurotransmitters and other biological molecules. Gene therapy also shows significant promise for treating diseases such as cancer, wherein the introduced gene acts to induce apoptosis, which is programmed cell death, or to otherwise shrink tumors.

The most significant problem heretofore encountered in the practical implementation of gene therapies, has been in delivering therapeutically effective amounts of genetic material into a target tissue. A number of approaches to the delivery problem have been implemented in the prior art. In one approach, a DNA plasmid including the therapeutic gene is injected into the patient. Some limited success has been achieved when this naked DNA is directly injected into a tumor; however, problems arise in obtaining access to the tumor and providing a continued delivery of the therapeutic material to the tumor site. Attempts have been made to inject the naked DNA intravenously; however, such attempts have not been very successful. In other instances, the therapeutic material is incorporated into a virus, typically in the form of a plasmid, and this virus is utilized to infect the target tissue. This approach is occasionally successful; however, the virus is often inactivated by the immune system or fails to infect the target tissue. Furthermore, the delivery of genes using viral vectors raises concerns regarding efficacy, efficiency, viral infection, toxicity, and delivery which limit the broader use of gene therapy delivered through viral vectors. Another approach has been to utilize mutated viruses specifically adapted to avoid immune system inactivation and/or better infect the target tissue. Another approach has been to utilize a mixture of a high molecular weight synthetic polymer with the DNA. Limited success has been achieved with such materials.

Thus, it will be appreciated that there is a need for a delivery system and method for providing gene therapy materials to target tissues. The system and methods should preferably be highly effective, simple to implement, the compounds should be highly stable in vivo, and reduce the need for repeated administration.

SUMMARY OF THE INVENTION

According to the present invention, there is provided a gene therapy material which includes a nucleic acid material and a carbohydrate wherein the carbohydrate preferably is a modified pectin.

Also in accordance with the present invention, there is provided a gene therapy material including a nucleic acid material, a carbohydrate material associated with the nucleic acid material, and a protective coating disposed about the carbohydrate material.

Also in accordance with the present invention, there is provided a method for treating a tumor of the type which has carbohydrate binding sites expressed on the surface thereof by providing a therapeutic material, incorporating the therapeutic material into a body of a modified pectin material so as to produce a therapeutic composition, and administering the therapeutic composition to a patient.

DETAILED DESCRIPTION OF THE INVENTION

In accord with the present invention, it has been found that carbohydrates can provide a very effective delivery vehicle for DNA and other such nucleic acid materials used in gene therapy. That is, a therapeutically effective amount of a therapeutic composition of the carbohydrate and the nucleic acid material can be administered to a patient or subject having a tumor to treat the tumor by causing a reduction and/or an elimination of the tumor from the patient. In the context of this disclosure, nucleic acid materials are meant to comprise genes, plasmids containing genes, other strands of DNA, RNA, and like materials. It has been found that when nucleic acid materials are mixed with, and preferably encapsulated by, carbohydrates, these materials are protected and efficiently delivered to target cells. Multiple genes can be delivered at one time and can be delivered in a single vector or in multiple vectors encapsulated by the carbohydrates of the present invention. The carbohydrate based gene therapy materials of the present invention have been found to be effective even when administered orally, although such materials could also be delivered intravenously or by direct injection to a target tissue (i.e. a tumor).

In the context of this disclosure, carbohydrates shall refer to any hexose or pentose structure and shall specifically include complex carbohydrates as well as simple carbohydrates. One particularly preferred carbohydrate which can be employed in the present invention is a modified citrus pectin material, and such materials are disclosed in U.S. patent application Ser. No. 08/024,487 filed Mar. 1, 1993 and U.S. patent application Ser. No. 08/819,356 filed Mar. 18, 1997 and is referred to herein as GBC-590. The modified citrus pectin material is non-toxic, stable for oral administration, has good uptake characteristics, stable in the circulation for days vs. hours, specifically targeted to tumors, and can be packaged for efficient uptake by tumor cells. The main chains of the modified citrus pectin have the structure

[-4)-α-D-GalpA-(1-4)-α-D-GalpA-(1-]$_n$-4)-α-D-GalpA-(1-2)-β-L-Rhap-(1-[-4)-α-D-GalpA-(1-4))-α-D-Galp-(1-] with minor structural features including
  (a) interrupted regions in rhamnogalacturonan chains (configurations and linkage types as above)
    —GalA-Rha-GalA-Rha-GalA-GalA-Rha-Rha-GalA-,
  (b) short side chains
    β-D-xylp-(1-3)-β-D-Galp-(1-2)-D-Xylp-(1-α-L-fucp-(1-2)-D-Xylp-(1-L-araf-(1-3)-D-Apif-(103)-D-Apif-(1-, and
  (c) extended side chains
    -4-β-D-Galp-(1-4)-β-D-Galp-(1-α-L-Araf-(1-5)-α-L-Araf-(1—
    3
    ↑
    1
    α-L-Araf.

The terms "patient" or "subject" as used herein mean all animals including humans. Examples of patients or subjects include humans, rodents, and monkeys.

Those skilled in the art are easily able to identify patients with cancer. For example, patients having malignant tumors in their bodies.

A "therapeutically effective amount" is an amount of a compound and/or composition of the present invention, that when administered to a patient or subject, causes the reduction and/or the elimination of a tumor in the patient or subject.

In accord with another embodiment of the invention, viral vectors such as modified or unmodified adenovirus, viral proteins or other portions of virus which carry gene therapy materials, can be encapsulated in carbohydrate materials in accord with the present invention. In this manner, the viral vectors are protected from inactivation and delivered more directly to target cells.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses such as adenoviruses or adeno-associated viruses (AAV), cosmids, plasmids, liposomes and other recombination vectors. The vectors can also contain elements for use in either prokaryotic or eukaryotic host systems. One of ordinary skill in the art will know which host systems are compatible with a particular vector.

The vectors in accordance with the present invention can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992); in Ausubel et al., Current Protocols in Molecular Biology, John Wiley and Sons, Baltimore, Md. (1989); Chang et al., Somatic Gene Therapy, CRC Press, Ann Arbor, Mich. (1995); Vega et al., Gene Targeting, CRC Press, Ann Arbor, Mich. (1995); Vectors: A Survey of Molecular Cloning Vectors and Their Uses, Butterworths, Boston, Mass. (1988); and Gilboa et al. (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for injection.

An alternate mode of administration of the gene therapy material of the present invention is by direct inoculation locally at the site of the disease or pathological condition or by inoculation into the vascular system supplying the tumor with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

In accord with the present invention, the nucleic acid material is mixed with the carbohydrate and is mildly sonicated. It is speculated that some degree of binding may take place in this combination, although binding is not believed to be essential to the invention. In particularly preferred embodiments, the nucleic acid material is encapsulated by a covering of the carbohydrate, and the carbohydrate-nucleic acid combination is most preferably configured as a relatively small micelle. In some instances, the micelles are further protected with a coating material, and one particularly preferred coating comprises chitin or chitosan, and the chitin or chitosan may be in the form of relatively short chain oligomeric material.

While the present invention can be employed in connection with a variety of different gene therapies and/or specific genes, one particular embodiment has specific utility in cancer therapies. The tyrosine kinase gene (CHK) has been found to be an effective gene therapy material for various cancers. CHK expression has been observed in many human primary tumors including ovarian carcinoma, breast carcinoma, astrocytoma, glioblastoma, pancreatic carcinoma, lung carcinoma, liver carcinoma, and renal carcinoma The CHK gene is up-regulated in many cancers and can suppress tumor development. In some instances the gene appears to induce apoptosis. In breast cancer, the gene has been found to antagonize growth-promoting signals mediated by Src and ErbB-2 tyrosine kinases. Applicant has further found that many tumor cells have sites thereon which actively bind carbohydrates thereto, and the CHK gene, via its stimulation of the production of tyrosine kinases, causes buildup of carbohydrate to occur on the surface of cancer cells. Based on these findings, Applicant has surmised that the CHK gene and carbohydrate materials of the present invention can interact beneficially to provide a gene therapy material for a variety of cancers. Other genes which can be used in the present invention include tumor suppressor genes including p53, angiostatic genes including angiostatin p60-hangio or endostatin p60-hendo, apoptotic genes including Bcl and Bax, and/or mixtures thereof.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intreperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chiorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar—agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and an preservatives, buffers, or propellants as may be required. Ophthalmic formulations, eye ointments, powders, and solution are also contemplated as being within the scope of this invention.

The compounds of the present invention can be administered to a patient at dosage levels in the range of about 1.9 mg/m² to about 40 mg/m² of carbohydrate combined with about 1.9 µg/m² to about 4 mg/m² of nucleic acid per day. For a normal human adult having a body weight of about 70 kilograms, a dosage in the range of about 0.05–1.06 mg/kg/day carbohydrate combined with about 0.00005–0.106 mg/kg/day is preferable. That is, the general ratio of the amount of carbohydrate to the amount of nucleic acid material is approximately 10:1 in the composition which is administered to the patient or subject. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

The examples presented below are intended to illustrate particular embodiments of the invention and are not intended to limit the scope of the specification, including the claims, in any way.

EXPERIMENTAL DATA

EXAMPLE 1

In a prophetic experimental series, a material is prepared comprising DNA, in the form of plasmids, incorporating the CHK gene. This DNA material is mixed with modified pectin of the type disclosed hereinabove and is sonicated to produce a micellular structure. These micelles are coated with chitosan. The material is administered orally to nude mice in which pancreatic tumors are previously established. It will be found that oral administration of this material can produce complete tumor remission in the mice. Tumor responsiveness to the orally administered material is hoped to be at least as good as the response to material directly injected into tumors. The orally administered material is easier to use, and provides a more sustained and widespread delivery. Oral administration of the DNA material alone, without the carbohydrate, should be ineffective.

EXAMPLE 2

Gene therapy studies using a CHK complex in a cancer treatment were performed. Cancer cells (MCF-7 and MCF-7/neo human breast cancer cell lines) were implanted in nude mice to form tumors. The body weight of the mice and tumor surface area were measured. After a tumor was formed, the mice were treated with an injection of CHK DNA through the tail vein for a week and were then observed for sixty days. A control group received no treatment. At the end of the observation period, twenty-four mice out of the thirty in one group of the treated population and twenty-three mice out of thirty mice in another treatment group were found to be completely free of cancer as shown in Table 1.

EXAMPLE 3

An experiment was carried out in order to determine the effect of GBC-590/CHK on PANC-1 tumor cell growth in nude mice. In this experiment, human PANC-1 cancer cells were implanted into nude mice. Tumors were formed a week after the initial implantation and then different treatments were performed on individual groupings. Treatment groups included no-treatment (control), treatment with the CHK gene alone, treatment with GBC-590 alone, and treatment with GBC-590 combined with the CHK gene in accordance with the present invention at various concentrations. The mice were injected with the different treatments through the tail vein for a week and then observations were made for a period of sixty days thereafter. The results indicated that the combination of GBC-590 and the CHK gene in accordance with the present invention dramatically inhibited tumor growth as shown in Table 2.

EXAMPLE 4

The effect of chitosan/CHK on PANC-1 tumor growth in nude mice was determined by the following experiment. In this experiment, human PANC-1 cancer cells were implanted into nude mice. The tumors were formed a week after the initial implantation and then a regimen of different treatments were performed. The treatment groups included no-treatment (control), treatment with the CHK gene alone, treatment with chitosan alone, and treatment with chitosan plus the CHK gene at various concentrations. The mice were either injected with the different treatments through the tail vein or were injected directly into the tumor site for a week and then were observed for a period of twenty-four days. The results, shown in Table 3, demonstrate that chitosan together with the CHK dramatically inhibited tumor growth when administered through intravenous injection.

As is demonstrated in the above Examples, the present invention provides a system for delivering gene therapy materials to tissue sites. The invention can be used in cancer therapies or to deliver other genetic materials to cells.

Yet another embodiments of the present invention will be readily apparent to one of skill in the art in view of the teachings presented herein. It is the following claims, including all equivalents, which define the scope of the invention.

TABLE 1

Gene therapy studies using CHK complex in a cancer treatment

| | Untreated | | | | Treated for 60 Days | | | |
|---|---|---|---|---|---|---|---|---|
| | MCF-7 Cells Alone | | MCF-7/neo cells | | MCF-7/CHK #10 | | MCF-7/CHK #5 | |
| | Grams | Std. Dev. +/− | Grams | Std. Dev. +/− | Grams | Std. Dev. +/− | Grams | Std. Dev. +/− |
| Body Weight | 26.1 | 0.4 | 25.9 | 0.1 | 26 | 0.1 | 25.3 | 0.2 |
| Tumor Surface Area (cm²) | 0.75 | 0.04 | 0.72 | 0.03 | 0.21 | 0.03 | 0.20 | 0.02 |
| Results | Remitted | Total Mice | Remitted | Total Mice | Remitted | Total Mice | Remitted | Total Mice |
| Mice with Tumor | 0 | 30 | 0 | 10 | 24 | 30 | 23 | 30 |
| % Mice Remitted | 0% | | 0% | | 80% | | 77% | |

TABLE 2

Effect of GBC-590/CHK on PANC-1 tumor cell growth in nude mice

| Treatment Group | Number of Mice | Tumor Size 60 Days After Treatment | Std. Dev. +/- |
|---|---|---|---|
| Control | 2 | mice died within 2 weeks with tumor size at 1500 | |
| CHK DNA alone | 4 | 396 | 45 |
| GBC-590 alone | 4 | 394.5 | 142.5 |
| GBC-590 + CHK (1:10) | 4 | 204 | 12 |
| GBC-590 + CHK (1:100) | 4 | 245 | 3 |
| GBC-590 + CHK (1:1000) | 4 | 489 | 129 |

TABLE 3

Effect of Chitosan/CHK on PANC-1 tumor cell growth in nude mice

| Treatment Group | Number of Mice | Tumor Size 60 Days After Treatment | Std. Dev. +/- |
|---|---|---|---|
| Control | 2 | 81 (very unhealthy) | 8 |
| CHK DNA alone I.V. injection | 2 | 10.5 | 2 |
| CHK DNA alone tumor injection | 2 | 154 | 10 |
| Chitosan I.V. injection | 2 | 34 | 2 |
| Chitosan tumor injection | 2 | 120 | 19 |
| Chitosan + CHK (1:10) I.V. injection | 4 | 12.5 | 0.5 |
| Chitosan + CHK (1:10) tumor injection | 4 | 52.5 | 21 |
| Chitosan + CHK (1:100) I.V. injection | 4 | 29 | 1 |
| Chitosan + CHK (1:100) tumor injection | 4 | 94.25 | 27 |

What is claimed is:

1. A composition comprising:
   modified citrus pectin and a nucleic acid material, said nucleic acid material being encapsulated by said modified citrus pectin.
2. The composition of claim 1, wherein said modified citrus pectin is a pH modified citrus pectin.
3. The composition of claim 1, wherein said nucleic acid material is DNA.
4. The composition of claim 1, wherein said nucleic acid material is RNA.
5. A composition comprising:
   modified pectin and a nucleic acid material, said nucleic acid material being encapsulated by said modified pectin.
6. The composition of claim 1, wherein said modified pectin is a pH modified pectin.
7. The composition of claim 1, wherein said nucleic acid material is DNA.
8. The composition of claim 1, wherein said nucleic acid material is RNA.

* * * * *